United States Patent
Inai et al.

(10) Patent No.: US 10,428,394 B2
(45) Date of Patent: Oct. 1, 2019

(54) METHOD OF PROMOTING PLANT GROWTH

(71) Applicants: IDEMITSU KOSAN CO., LTD., Chiyoda-ku (JP); SDS BIOTECH K.K., Chuo-ku (JP)

(72) Inventors: Koji Inai, Tsukuba (JP); Motoki Tanaka, Tsukuba (JP); Yusuke Amaki, Tsukuba (JP)

(73) Assignees: IDEMITSU KOSAN CO., LTD., Chiyoda-ku (JP); SDS BIOTECH K.K., Chuo-ku (JP)

( * ) Notice: Subject to any disclaimer, the term of this patent is extended or adjusted under 35 U.S.C. 154(b) by 0 days.

(21) Appl. No.: 15/029,814

(22) PCT Filed: Oct. 14, 2014

(86) PCT No.: PCT/JP2014/077306
§ 371 (c)(1),
(2) Date: Apr. 15, 2016

(87) PCT Pub. No.: WO2015/056666
PCT Pub. Date: Apr. 23, 2015

(65) Prior Publication Data
US 2016/0237512 A1    Aug. 18, 2016

(30) Foreign Application Priority Data
Oct. 17, 2013   (JP) .................................. 2013-216834

(51) Int. Cl.
*A01N 63/00* (2006.01)
*C12N 1/20* (2006.01)
*C12R 1/07* (2006.01)
*A01G 7/00* (2006.01)

(52) U.S. Cl.
CPC .............. *C12R 1/07* (2013.01); *A01G 7/00* (2013.01); *A01N 63/00* (2013.01); *C12N 1/20* (2013.01)

(58) Field of Classification Search
None
See application file for complete search history.

(56) References Cited

U.S. PATENT DOCUMENTS 5,670,365 A   9/1997  Feitelson
6,060,051 A   5/2000  Heins et al.
6,291,426 B1  9/2001  Heins et al.
2004/0265292 A1  12/2004  Watanabe et al.
2011/0212835 A1*  9/2011  Bais ..................... A01N 63/00
                                                    504/100
2012/0149571 A1*  6/2012  Kloepper ............... A01N 63/00
                                                    504/117
2014/0179528 A1  6/2014  Amaki et al.

FOREIGN PATENT DOCUMENTS

| CN | 1715396 A | 1/2006 |
|---|---|---|
| CN | 101845409 A | 9/2010 |
| JP | 2955655 B2 | 10/1999 |
| JP | 2000-135096 A | 5/2000 |
| JP | 3471811 A | 12/2003 |
| JP | 3471815 B2 | 12/2003 |
| JP | 2006-304684 A | 11/2006 |
| JP | 4071036 B2 | 4/2008 |
| JP | 2009-247302 A | 10/2009 |
| JP | 4359653 B2 | 11/2009 |
| JP | 5198690 B2 | 5/2013 |
| WO | 96/32840 A1 | 10/1996 |
| WO | 2012/161160 A1 | 11/2012 |

OTHER PUBLICATIONS

Xiao et al., Pedosphere 23(2): 160-168, 2013.*
International Preliminary Report on Patentability and Written Opinion dated Apr. 28, 2016 in PCT/JP2014/077306 (submitting English translation only).
AB531397, Database, [online], URL, <http://www.ebi.ac.uk/ena/data/view/AB531397&display=text>, Nov. 11, 2009, (2 pages).
AB188212, Database, [online], URL, <http://getentry.ddbj.nig.ac.jp/getentry/na/AB168212/?filetype=html>, Oct. 8, 2005, (1 page).
International Search Report dated Jan. 20, 2015 in PCT/JP2014/077306 filed Oct. 14, 2014.
Partial Supplementary Search Report dated Feb. 27, 2017 in European Patent Application No. 14854641.9.
Japanese Office Action dated Aug. 7, 2018, in Japanese Patent Application No. 2015-542611 (with English Translation).
Narihiro, T., et al., Activity and Phylogenetic Composition of Proteolytic Bacteria in Mesophilic Fed-batch Garbage Composters, Microbes and Environments, vol. 19, No. 4, pp. 292-300., 2004.
Office Action dated Feb. 3, 2019, in Chinese Patent Application No. 201480057082.1, filed Oct. 14, 2014 (with English Translation).

* cited by examiner

*Primary Examiner* — David W Berke-Schlessel
(74) *Attorney, Agent, or Firm* — Oblon, McClelland, Maier & Neustadt, L.L.P.

(57) ABSTRACT

A microorganism selected from the group consisting of a *Bacillus* sp. ITB090 strain (NITE BP-01725), a *Bacillus* sp. ITB100 strain (NITE BP-01726), and a *Bacillus* sp. ITB105 strain (NITE BP-01727), or a variant strain derived therefrom is used to control plant diseases, control nematodes, promote plant growth, and the like.

20 Claims, No Drawings
Specification includes a Sequence Listing.

SEQUENCE LISTING

<160> NUMBER OF SEQ ID NOS: 4

<210> SEQ ID NO 1
<211> LENGTH: 1511
<212> TYPE: DNA
<213> ORGANISM: Bacillus sp. ITB090

<400> SEQUENCE: 1

```
gagtttgatc ctggctcagg atgaacgctg gcggcgtgcc taatacatgc aagtcgagcg      60
aaccgattaa gagcttgctc ttaagaagtt agcggcggac gggtgagtaa cacgtaggta     120
acctgcctat aagactggga taactccggg aaaccggggc taataccgga taacattttg     180
caccgcatgg tgcgaaattg aaaggcggct tcggctgtca cttatagatg gacctgcggc     240
gcattagcta gttggtgagg taacggctca ccaaggcgac gatgcgtagc cgacctgaga     300
gggtgatcgg ccacactggg actgagacac ggcccagact cctacgggag gcagcagtag     360
ggaatcttcc gcaatggacg aaagtctgac ggagcaacgc cgcgtgagcg atgaaggcct     420
tcgggtcgta aagctctgtt gttagggaag aacaagtgct agttgaataa gctggcacct     480
tgacggtacc taaccagaaa gccacggcta actacgtgcc agcagccgcg gtaatacgta     540
ggtggcaagc gttatccgga attattgggc gtaaagcgcg cgcaggtggt ttcttaagtc     600
tgatgtgaaa gcccacggct caaccgtgga gggtcattgg aaactgggag acttgagtgc     660
agaagaggaa agtggaattc catgtgtagc ggtgaaatgc gtagagatat ggaggaacac     720
cagtggcgaa ggcgactttc tggtctgcaa ctgacactga ggcgcgaaag cgtggggagc     780
aaacaggatt agataccctg gtagtccacg ccgtaaacga tgagtgctaa gtgttagagg     840
```

```
gtttccgccc tttagtgctg aagttaacgc attaagcact ccgcctgggg agtacggccg      900
caaggctgaa actcaaagga attgacgggg gcccgcacaa gcggtggagc atgtggttta      960
attcgaagca acgcgaagaa ccttaccagg tcttgacatc ctctgacaac cctagagata     1020
gggcttcccc ttcggggca gagtgacagg tggtgcatgg ttgtcgtcag ctcgtgtcgt     1080
gagatgttgg gttaagtccc gcaacgagcg caacccttga tcttagttgc catcattaag     1140
ttgggcactc taaggtgact gccggtgaca accggagga aggtggggat gacgtcaaat      1200
catcatgccc cttatgacct gggctacaca cgtgctacaa tggacggtac aaagagtcgc     1260
aagaccgcga ggtggagcta atctcataaa accgttctca gttcggattg taggctgcaa     1320
ctcgcctaca tgaagctgga atcgctagta atcgcggatc agcatgccgc ggtgaatacg     1380
ttcccgggcc ttgtacacac cgcccgtcac accacgagag tttgtaacac ccgaagtcgg     1440
tggggtaacc ttttggagcc agccgcctaa ggtgggacag atgattgggg tgaagtcgta     1500
acaaggtagc c                                                          1511

<210> SEQ ID NO 2
<211> LENGTH: 1510
<212> TYPE: DNA
<213> ORGANISM: Bacillus sp. ITB100

<400> SEQUENCE: 2
gagtttgatc ctggctcagg acgaacgctg gcggcgtgcc taatacatgc aagtcgagcg       60
gacagatggg agcttgctcc ctgatgttag cggcggacgg gtgagtaaca cgtgggtaac      120
ctgcctgtaa gactgggata actccgggaa accggggcta ataccggatg gttgtytgaa      180
ccgcatggtt cagacataaa aggtggcttc ggctaccact tacagatgga cccgcggcgc      240
attagctagt tggtgaggta acggctcacc aaggcgacga tgcgtagccg acctgagagg      300
gtgatcggcc acactgggac tgagacacg cccagactcc tacgggaggc agcagtaggg      360
aatcttccgc aatggacgaa agtctgacgg agcaacgccg cgtgagtgat gaaggttttc      420
ggatcgtaaa gctctgttgt tagggaagaa caagtgccgt tcaaataggg cggcaccttg      480
acggtaccta accagaaagc cacggctaac tacgtgccag cagccgcggt aatacgtagg      540
tggcaagcgt tgtccggaat tattgggcgt aaagggctcg caggcggttt cttaagtctg      600
atgtgaaagc ccccggctca accggggagg gtcattggaa actggggaac ttgagtgcag      660
aagaggagag tggaattcca cgtgtagcgg tgaaatgcgt agagatgtgg aggaacacca      720
gtggcgaagg cgactctctg gtctgtaact gacgctgagg agcgaaagcg tggggagcga      780
acaggattag ataccctggt agtccacgcc gtaaacgatg agtgctaagt gttagggggt      840
ttccgcccct tagtgctgca gctaacgcat taagcactcc gcctgggag tacggtcgca      900 agactgaaac tcaaaggaat tgacggggc cgcacaagc ggtggagcat gtggtttaat      960
tcgaagcaac gcgaagaacc ttaccaggtc ttgacatcct ctgacaatcc tagagatagg     1020
acgtccccct cggggcaga gtgacaggtg gtgcatggtt gtcgtcagct cgtgtcgtga     1080
gatgttgggt taagtcccgc aacgagcgca acccttgatc ttagttgcca gcattcagtt     1140
gggcactcta agtgactgc cggtgacaaa ccggaggaag gtgggatga cgtcaaatca      1200 tcatgcccct tatgacctgg ctacacacg tgctacaatg gacagaacaa agggcagcga     1260
aaccgcgagg ttaagccaat cccacaaatc tgttctcagt tcggatcgca gtctgcaact     1320
cgactgcgtg aagctggaat cgctagtaat cgcggatcag catgccgcgg tgaatacgtt     1380
```

```
cccgggcctt gtacacaccg cccgtcacac cacgagagtt tgtaacaccc gaagtcggtg    1440
aggtaacctt tatggagcca gccgccgaag gtgggacaga tgattggggt gaagtcgtaa    1500
caaggtagcc                                                           1510

<210> SEQ ID NO 3
<211> LENGTH: 1510
<212> TYPE: DNA
<213> ORGANISM: Bacillus sp. ITB105

<400> SEQUENCE: 3
gagtttgatc ctggctcagg acgaacgctg gcggcgtgcc taatacatgc aagtcgagcg      60
gacagatggg agcttgctcc ctgatgttag cggcggacgg gtgagtaaca cgtgggtaac     120
ctgcctgtaa gactgggata actccggaaa accggggcta ataccggatg gttgtttgaa     180
ccgcatggtt caaacataaa aggtggcttc ggctaccact tacagatgga cccgcggcgc     240
attagctagt tggtgaggta acggctcacc aaggcaacga tgcgtagccg acctgagagg     300
gtgatcggcc acactgggac tgagacacgg cccagactcc tacgggaggc agcagtaggg     360
aatcttccgc aatggacgaa agtctgacgg agcaacgccg cgtgagtgat gaaggttttc     420
ggatcgtaaa gctctgttgt tagggaagaa caagtaccgt tcgaataggg cggtaccttg     480
acggtaccta accagaaagc cacggctaac tacgtgccag cagccgcggt aatacgtagg     540
tggcaagcgt tgtccggaat tattgggcgt aaagggctcg caggcggttt cttaagtctg     600
atgtgaaagc cccggctcaa ccggggaggg tcattggaaa ctgggaac ttgagtgcag       660 aagaggagag tggaattcca cgtgtagcgg tgaaatgcgt agagatgtgg aggaacacca     720
gtggcgaagg cgactctctg gtctgtaact gacgctgagg agcgaaagcg tggggagcga     780
acaggattag ataccctggt agtccacgcc gtaaacgatg agtgctaagt gttaggggt      840 ttccgcccct tagtgctgca gctaacgcat taagcactcc gcctggggag tacggtcgca     900
agactgaaac tcaaaggaat tgacggggc cgcacaagc ggtggagcat gtggtttaat       960
tcgaagcaac gcgaagaacc ttaccaggtc ttgacatcct ctgacaatcc tagagatagg    1020
acgtcccctt cggggggcaga gtgacaggtg gtgcatggtt gtcgtcagct cgtgtcgtga    1080
gatgttgggt taagtcccgc aacgagcgca acccttgatc ttagttgcca gcattcagtt    1140
gggcactcta aggtgactgc cggtgacaaa ccggaggaag gtgggatga cgtcaaatca     1200 tcatgcccct tatgacctgg gctacacacg tgctacaatg gacagaacaa agggcagcga    1260
aaccgcgagg ttaagccaat cccacaaatc tgttctcagt tcggatcgca gtctgcaact    1320
cgactgcgtg aagctggaat cgctagtaat cgcggatcag catgccgcgg tgaatacgtt    1380
cccgggcctt gtacacaccg cccgtcacac cacgagagtt tgtaacaccc gaagtcggtg    1440
aggtaacctt ttaggagcca gccgccgaag gtgggacaga tgattggggt gaagtcgtaa    1500
caaggtagcc                                                           1510

<210> SEQ ID NO 4
<211> LENGTH: 1496
<212> TYPE: DNA
<213> ORGANISM: Bacillus sp. ITB117

<400> SEQUENCE: 4
gagtttgatc ctggctcagg acgaacgctg gcggcgtgcc taatacatgc aagtcgagcg      60
agkstcttcg gasstagcg gcggacgggt gagtaacacg taggcaacct gcctctcaga     120
ctgggataac ataggaaac ttatgctaat accggatagg tttyggaty gcatgatccg       180
```

-continued

```
aaaagaaaag atggcttcgg ctatcactgg gagatgggcc tgcggcgcat tagctagttg    240
gtggggtaac ggcctaccaa ggcgacgatg cgtagccgac ctgagagggt gaccggccac    300
actgggactg agacacggcc cagactccta cgggaggcag cagtagggaa ttttccacaa    360
tggacgaaag tctgatggag caacgccgcg tgaacgatga aggtcttcgg attgtaaagt    420
tctgttgtta gggacgaata agtaccgttc gaatagggcg gtaccttgac ggtacctgac    480
gagaaagcca cggctaacta cgtgccagca gccgcggtaa tacgtaggtg gcaagcgttg    540
tccggattta ttgggcgtaa agcgcgcgca ggcggctatg taagtctggt gttaaagccc    600
ggrgctcaac yccggttcgc atcggaaact gtgtagcttg agtgcagaag aggaaagcgg    660
tattccacgt gtagcggtga aatgcgtaga gatgtggagg aacaccagtg gcgaaggcgg    720
ctttctggtc tgtaactgac gctgaggcgc gaaagcgtgg ggagcaaaca ggattagata    780
ccctggtagt ccacgccgta aacgatgagt gctaggtgtt gggggtttca ataccctcag    840
tgccgcagct aacgcaataa gcactccgcc tggggagtac gctcgcaaga gtgaaactca    900
aaggaattga cggggcccg cacaagcggt ggagcatgtg gtttaattcg aagcaacgcg    960 aagaaccttta ccaggtcttg acatcccgct gaccgctctg gagacagagc ttcccttcgg   1020
ggcagcggtg acaggtggtg catggttgtc gtcagctcgt gtcgtgagat gttgggttaa   1080
gtcccgcaac gagcgcaacc cttatcttta gttgccagca ttcagttggg cactctagag   1140
agactgccgt cgacaagacg gaggaaggcg gggatgacgt caaatcatca tgcccttat    1200 gacctgggct acacacgtgc tacaatggtt ggtacaacgg gatgctacct cgcgagagga   1260
cgccaatctc ttaaaaccaa tctcagttcg gattgtaggc tgcaactcgc ctacatgaag   1320
tcggaatcgc tagtaatcgc ggatcagcat gccgcggtga atacgttccc gggccttgta   1380
cacaccgccc gtcacaccac gggagtttgc aacacccgaa gtcggtgagg taaccgcaag   1440
gagccagccg ccgaaggtgg ggtagatgac tggggtgaag tcgtaacaag gtagcc       1496
```

METHOD OF PROMOTING PLANT GROWTH

TECHNICAL FIELD

The present invention relates to a novel microorganism useful for plant disease control, nematode control, and plant growth promotion. The present invention further relates to use of the novel microorganism as a microbiological formulation for improvement of resistance to a plant pathogen, nematode control, and promotion of plant growth.

BACKGROUND ART

As a control method of a plant disease a biological control technology not using a conventional chemical pesticide but using a microorganism isolated from the natural world has drawn attention, and several microbial pesticides have been commercialized. However, existing microbial pesticides have drawbacks that the effect is not stable and a range of applicable diseases is rather limited compared to a chemical pesticide. Due to such a situation, there is a demand for a novel microbial pesticide applicable to a new disease and exhibiting a stable controlling effect.

Examples of plant disease controlling agents using a microorganism, which have been registered and used as a microbial pesticide, include a *Talaromyces flavus* agent, a *Pseudomonas fluorescens* agent, a nonpathogenic *Erwinia carotovora* agent, a *Trichoderma atroviride* agent, a *Bacillus simplex* agent, and a *Bacillus subtilis* agent.

As a nematode controlling agent using a microorganism, a *Pasteuria penetrans* agent, and a *Monacrosporium phymatophagum* agent have been registered and used as a microbial pesticide.

A plant disease controlling agent using a bacterium belonging to *Bacillus amyloliquefaciens* has been disclosed in Japanese Patent No. 2955655 (Patent Literature 1). The active ingredient of the plant disease controlling agent is a product of a microorganism, and the bacterium itself is not utilized as a pesticide. Further, there is no description at all about promotion of plant growth, nor nematode control.

Meanwhile, a plant disease controlling agent using a bacterium belonging to *Bacillus amyloliquefaciens* has been disclosed in Japanese Patent No. 5198690 (Patent Literature 2), but the bacterium is categorically different from a strain according to the present invention.

Further, a microbial pesticide, which is able to control simultaneously a filamentous fungal disease and a bacterial disease, and in which a living bacterial cell itself is effective, has been disclosed in Japanese Unexamined Patent Application Publication No. 2009-247302 (Patent Literature 3), but there is no description about promotion of plant growth, nor nematode control.

A plant disease controlling agent using a bacterium belonging to the genus *Bacillus*, which is able to be applied to a wide range of plant diseases and effective to a corn rootworm, has been disclosed in Japanese Patent No. 3471815 (Patent Literature 4, WO98/050422), but there is no description about promotion of plant growth, nor nematode control.

Further, a *Bacillus* sp. D747 strain, which can be applied to plant disease control and insect pest control, has been disclosed in Japanese Patent No. 4071036 (Patent Literature 5, US2004/265292), but there is no description about promotion of plant growth, nor nematode control.

A nematode controlling agent using a bacterium belonging to the genus *Bacillus* has been disclosed in Japanese Patent No. 3471811 (Patent Literature 6, WO96/032840). The active ingredient of the nematode controlling agent is a bacterium of a *Bacillus firmus* strain or a spore thereof having nematicidal activity, but there is no description about promotion of plant growth, nor plant disease control.

A nematode controlling method with a nematicidal toxin produced by a novel *Bacillus thuringiensis* strain has been disclosed in Japanese Patent No. 4359653 (Patent Literature 7, WO1997/012980), but there is no description about promotion of plant growth, nor plant disease control.

Although in agriculture a chemical fertilizer is an important agricultural material influencing the yield of a crop, 30 to 50% of a chemical fertilizer component applied is diffused into the environment without being utilized by a crop to cause eutrophication of a river, pollution of groundwater or the like. In this connection, since a large amount of a fossil fuel is consumed in producing a chemical fertilizer, costs of a chemical fertilizer have been increasing in step with the escalating fossil fuel prices. Further, nitrogen oxide ($NO_X$), which is a degradation product of a nitrogen fertilizer, is said to have a greenhouse effect approx. 300 times as strong as carbon dioxide, and there is growing concern about global warming therefrom. Meanwhile, future food shortage is anticipated in view of the global population increase, and therefore use of a material for increasing the crop productivity is essential and there is an increasing need for an environmentally more friendly material substituting a conventional chemical fertilizer.

In light of such circumstances, researches for increasing the farm product yield utilizing a soil microorganism have been carried out mainly with respect to broad range of *Rhizobium* bacteria (root nodule bacteria), *Pseudomonas* bacteria, and *Bacillus* bacteria, however only few have been put into practical use due to limited effectiveness.

As described above, there has been a strong demand for a microorganism, which can reduce a load on the environment without relying upon a chemical pesticide and a chemical fertilizer, and control a plant disease and a nematode, as well as promote plant growth.

PRIOR ART DOCUMENTS

Patent Literature

[Patent Literature 1] Japanese Patent No. 2955655
[Patent Literature 2] Japanese Patent No. 5198690
[Patent Literature 3] Japanese Unexamined Patent Application Publication No. 2009-247302
[Patent Literature 4] Japanese Patent No. 3471815
[Patent Literature 5] Japanese Patent No. 4071036
[Patent Literature 6] Japanese Patent No. 3471811
[Patent Literature 7] Japanese Patent No. 4359653

SUMMARY OF THE INVENTION

Problems to be Solved by the Invention

An object of the present invention is to provide a novel microorganism having a plant disease controlling action, a nematode controlling action, and a plant growth promoting action.

Another object of the present invention is to provide a plant disease controlling agent, a nematode controlling agent, and a plant growth promoting agent usable as a biological pesticide (microbiological formulation) containing the microorganism as an effective bacterium.

Means for Solving the Problems

The inventors conducted diligently investigations in order to attain the objects to succeed in isolation of a *Bacillus* sp. ITB090 strain (NITE BP-01725), a *Bacillus* sp. ITB100 strain (NITE BP-01726), a *Bacillus* sp. ITB105 strain (NITE BP-01727), and a *Bacillus* sp. ITB117 strain (NITE P-01728), (hereinafter the microorganisms including variants thereof are occasionally referred to collectively as a "microorganism according to the present invention") and to find that the same have a controlling action on plural kinds of plant diseases, a nematode controlling action, and a plant growth promoting action, thereby completing the present invention.

Namely, the present invention includes the following.

[1] A microorganism selected from the group consisting of a *Bacillus* sp. ITB090 strain (NITE BP-01725), a *Bacillus* sp. ITB100 strain (NITE BP-01726), and a *Bacillus* sp. ITB105 strain (NITE BP-01727), or a variant strain derived therefrom.

[2] The microorganism or the variant strain according to [1], wherein the *Bacillus* sp. ITB090 strain (NITE BP-01725) has a 16S rDNA shown by the nucleotide sequence of SEQ ID NO: 1, a variant of the *Bacillus* sp. ITB090 strain (NITE BP-01725) has a 16S rDNA shown by a nucleotide sequence having a nucleotide identity of 99.5% or more with the nucleotide sequence of SEQ ID NO: 1, the *Bacillus* sp. ITB100 strain (NITE BP-01726) has a 16S rDNA shown by the nucleotide sequence of SEQ ID NO: 2, a variant of the *Bacillus* sp. ITB100 strain (NITE BP-01726) has a 16S rDNA shown by a nucleotide sequence having a nucleotide identity of 99.5% or more with the nucleotide sequence of SEQ ID NO: 2, the *Bacillus* sp. ITB105 strain (NITE BP-01727) has a 16S rDNA shown by the nucleotide sequence of SEQ ID NO: 3, and a variant of the *Bacillus* sp. ITB105 strain (NITE BP-01727) has a 16S rDNA shown by a nucleotide sequence having a nucleotide identity of 99.5% or more with the nucleotide sequence of SEQ ID NO: 3.

[3] A bacterial cell or a culture product of the microorganism or the variant strain according to [1] or [2].

[4] A microbiological formulation comprising the microorganism or the variant strain according to [1] or [2] or the bacterial cell or the culture product according to [3].

[5] The microbiological formulation according to [4], which is a plant growth promoting agent.

[6] The microbiological formulation according to [4], which is a plant disease controlling agent.

[7] The microbiological formulation according to [4], which is a nematode controlling agent.

[8] A method of promoting a plant growth, comprising a step for treating a plant or a soil with the bacterial cell or the culture product according to [3] or the microbiological formulation according to [5].

[9] A method of controlling a plant disease, comprising a step for treating a plant or a soil with the bacterial cell or the culture product according to [3] or the microbiological formulation according to [6].

[10] A method of controlling a nematode, comprising a step for treating a plant or a soil with the bacterial cell or the culture product according to [3] or the microbiological formulation according to [7].

[11] A cultivation method of a plant, comprising a step for treating a plant with the bacterial cell or the culture product according to [3] or the microbiological formulation according to any of [4] to [7].

Effect of the Invention

Since a microorganism according to the present invention has a controlling action on plural kinds of plant diseases, a nematode controlling action, and a plant growth promoting action, it does not rely on a chemical pesticide and a chemical fertilizer, and can be used as an effective microbiological formulation with little environmental load.

MODE FOR CARRYING OUT THE INVENTION

The present invention will be described below in detail.

A microorganism according to the present invention is the ITB090 strain (NITE BP-01725), the ITB100 strain (NITE BP-01726), the ITB105 strain (NITE BP-01727), the ITB117 strain (NITE P-01728), or a variant strain therefrom.

The ITB090 strain (NITE BP-01725) was identified as *Bacillus* sp. based on a sequence analysis of a 16S rRNA gene (SEQ ID NO: 1). The strain was deposited with Biological Resource Center (NBRC) of National Institute of Technology and Evaluation (NITE) at 2-5-8 Kazusakamatari, Kisarazu-shi, Chiba 292-0818, Japan, under accession number NITE P-01725 as of Oct. 17, 2013. It was then converted to an international deposit under the provisions of Budapest Treaty and received an accession number of NITE BP-01725.

The strain has bacteriological characters as follows:
(1) Morphological character
   Form: bacillary
   Size: width 1.0 μm, length 1.5 to 2.5 μm
   Motility: +
   Existence of spore: +
(2) Cultural character
   Culture medium: nutrient agar (30° C.)
   Shape: round
   Color tone: cream color
(3) Physiological character
   Gram staining: +

The ITB100 strain (NITE BP-01726) was identified as *Bacillus* sp. based on a sequence analysis of a 16S rRNA gene (SEQ ID NO: 2). The strain was deposited with Biological Resource Center (NBRC) of National Institute of Technology and Evaluation (NITE) at 2-5-8 Kazusakamatari, Kisarazu-shi, Chiba 292-0818, Japan, under accession number NITE P-01726 as of Oct. 17, 2013. It was then converted to an international deposit under the provisions of Budapest Treaty and received an accession number of NITE BP-01726.

The strain has bacteriological characters as follows:
(1) Morphological character
   Form: bacillary
   Size: width 0.8 to 0.9 μm, length 1.5 to 2.0 μm
   Motility: +
   Existence of spore: +
(2) Cultural character
   Culture medium: nutrient agar (30° C.)
   Shape: round
   Color tone: cream color
(3) Physiological character
   Gram staining: +

The ITB105 strain (NITE BP-01727) was identified as *Bacillus* sp. based on a sequence analysis of a 16S rRNA gene (SEQ ID NO: 3). The strain was deposited with Biological Resource Center (NBRC) of National Institute of Technology and Evaluation (NITE) at 2-5-8 Kazusakamatari, Kisarazu-shi, Chiba 292-0818, Japan, under accession number NITE P-01727 as of Oct. 17, 2013. It was then converted to an international deposit under the provisions of Budapest Treaty and received an accession number of NITE BP-01727.

The strain has bacteriological characters as follows:
(1) Morphological character
  Form: bacillary
  Size: width 0.8 to 0.9 μm, length 1.5 to 2.0 μm
  Motility: +
  Existence of spore: +
(2) Cultural character
  Culture medium: nutrient agar (30° C.)
  Shape: round
  Color tone: cream color
(3) Physiological character
  Gram staining: +

The ITB117 strain (NITE P-01728) was identified as *Bacillus* sp. based on a sequence analysis of a 16S rRNA gene (SEQ ID NO: 4). The strain was deposited with Biological Resource Center (NBRC) of National Institute of Technology and Evaluation (NITE) at 2-5-8 Kazusakamatari, Kisarazu-shi, Chiba 292-0818, Japan, under accession number NITE P-01728 as of Oct. 17, 2013.

The strain has bacteriological characters as follows:
(1) Morphological character
  Form: bacillary
  Size: width 0.8 to 0.9 μm, length 1.5 to 2.5 μm
  Motility: +
  Existence of spore: +
(2) Cultural character
  Culture medium: nutrient agar (30° C.)
  Shape: round
  Color tone: cream color
(3) Physiological character
  Gram staining: +

As for a variant strain derived from ITB090 (NITE BP-01725), ITB100 (NITE BP-01726), ITB105 (NITE BP-01727), or ITB117 strain (NITE P-01728), a spontaneous mutant, an induced mutant having used ultraviolet light irradiation, X-ray irradiation, or amutagenic agent (e.g. N-methyl-N-nitro-N-nitrosoguanidine), and a polyploidized cell therefrom are exemplified. In particular, a variant strain whose 16S rDNA has a nucleotide identity of 99.5% or more with respective wild-type 16S rDNA can be used preferably. The above-mentioned variant strains are included in a microorganism according to the present invention, insofar as they maintain the plant disease controlling action, the nematode controlling action, and the plant growth promoting action. In this connection, to maintain the plant disease controlling action, the nematode controlling action, and the plant growth promoting action means that any one of the actions is 80% or more compared to a parent strain.

As for a culture method of a microorganism according to the present invention, a publicly known means, such as a static culture including a solid medium, and a liquid culture, can be applied, and there is no particular restriction on the type of a culture medium or culture conditions, insofar as the bacterium can live and proliferate. Examples of a culture medium include a general culture medium, such as a meat extract medium, as well as a culture medium, containing glucose, peptone, or a yeast extract. Further, in addition to a liquid culture medium, a solid culture medium containing agar, such as a slant culture medium and a plate culture medium, may be used. A culture may be carried out in 2 stages of a seed culture and a main culture.

Although any carbon source for a culture medium may be applied insofar as it can be utilized by the above strain, specific examples thereof include glucose, galactose, lactose, sucrose, maltose, a malt extract, molasses, a starch syrup, and starch hydrolysis products.

Also as a nitrogen source for a culture medium, a material containing an organic nitrogen, such as peptone, a meat extract, a yeast extract, a soybean flour, and a corn steep liquor, as well as various synthetic or natural products, which the strain can utilize, may be applied.

Further, as in the usual manner for culturing a microorganism, an inorganic salt, such as a common salt and a phosphate, a salt of a metal, such as calcium, magnesium, and iron, and a micronutrient source, such as a vitamin and an amino acid, may be added according to need.

A culture can be performed under an aerobic condition by a shake culture, an aeration culture, or the like. The culture temperature is from 20 to 40° C., and preferably from 25 to 35° C., the pH is from 5 to 8, and preferably from 6 to 7, and the culture period is from 1 to 4 days, and preferably from 2 to 3 days.

A "culture product" according to the present invention includes, for example, a culture medium, or a culture solution containing bacterial cells after a culture of a microorganism according to the present invention, or a concentrate thereof.

A microbiological formulation containing a microorganism according to the present invention or a culture product thereof can be used as, for example, a plant disease controlling agent, a nematode controlling agent, and/or a plant growth promoting agent.

A microbiological formulation according to the present invention is preferably applied to a plant, and specific examples thereof include cereal crops, such as rice, wheat and corn; vegetables, such as carrot, cucumber, daikon radish, pumpkin, lettuce, eggplant, tomato, cabbage, potato, Chinese cabbage, crown daisy, Japanese mustard spinach, bell pepper, green onion, onion, ginger, garlic, and strawberry; mushrooms, such as shiitake mushroom; fruit trees, such as kaki, pear, mandarin orange, grape, apple, and peach; flowers and ornamental plants, such as chrysanthemum, tulip, and rose; and beans, such as soybean, sesame, and peanut.

"Plant disease control" means herein a function of preventing or curing a plant disease.

"Preventing a plant disease" means herein that the incidence rate of a plant, to which a controlling agent was applied, is lower than the incidence rate of a plant, to which a controlling agent was not applied, when a plant is cultivated, in the case of a soil disease, with a soil containing a pathogen that can infect the plant for a certain time period. Meanwhile, in the case of a stem and leaf disease, the term means that the incidence rate of a plant, to which a controlling agent was applied, is lower than the incidence rate of a plant, to which a controlling agent was not applied, when the plant is inoculated with a pathogen that can infect the plant and cultivated for a certain time period. Further, "curing a plant disease" means that the degree of illness of a plant, to which a controlling agent was applied, is mitigated compared to the degree of illness of a plant, to which a controlling agent was not applied, when plants infected with a disease are cultivated for a certain time period.

Although there is no particular restriction on a "plant disease" according to the present invention, insofar as it is a plant disease, on which a microorganism according to the present invention can exert a controlling effect, a plant disease caused by infection of a plant with a pathogen is preferable, and a stem and leaf disease and a soil disease is more preferable.

Examples of a stem and leaf disease as a control target according to the present invention include, but not limited to, a damping-off disease, an *Alternaria* blotch disease, anthracnose, a blast disease, a gray mold disease, and a powdery mildew disease.

A soil disease as a control target according to the present invention is preferably a soilborne disease, and more particularly a soil disease caused by any one or more of, but not limited to, a *Fusarium* genus fungus, a *Gaeumannomyces* genus fungus, a *Rhizoctonia* genus fungus, a *Pythium* genus fungus, a *Verticillium* genus fungus, a *Phytophthora* genus fungus, a *Sclerotium* genus fungus, a *Corticium* genus fungus, a *Plasmodiophora* genus fungus, a *Rhizopus* genus fungus, a *Trichoderma* genus fungus, a *Microdochium* genus fungus, and a *Sclerotinia* genus fungus. Specific examples of such a soil disease include, but not limited to, a *Pythium* lawn disease, and a lettuce root rot disease.

Although it is preferable that the microorganism is applied to a plant before suffering such a plant disease for preventing the disease, it may also be applied to a plant suffering from the plant disease for curing the same.

"Plant growth promotion" according to the present invention means an effect leading to increase in yield or improvement of quality in the fields of agriculture and horticulture as the results of promotion of increase in the leaf area of a cultivated plant, increase in photosynthesis power, increase in chlorophyll, increase in the weight and thickness of a terrestrial stem and leaf, increase in the weight of a subterrestrial part (root, etc.), and increase in outgrowth of a root, and/or increase in the number and weight of grains and fruits, by a treatment of a plant with a microorganism or a microbiological formulation according to the present invention by a method, such as a ground application of a liquid, a ground application of a solid, an aerial application of a liquid, an aerial application of a solid, a water surface application, an intra-institution application, a soil incorporation application, a soil irrigation application, a nursery box method, an individual flower treatment, a plant foot treatment, etc., or by a surface treatment of a seed or a seed potato for a cultivated plant (powder coating of a seed, an immersion treatment, a painting treatment, etc.).

Specific examples of pathogen of diseases that a microorganism according to the present invention can control include, but not limited to, with respect to rice *Pyricularia oryzae, Cochliobolus miyabeanus, Rhizoctonia solani,* and *Gibberella fujikuroi*; with respect to wheat and barley, *Erysiphe graminis* f. sp. *hordei, Erysiphe graminis* f. sp. *tritici, Puccinia striiformis, Puccinia graminis, Puccinia recondita* f. sp. *tritici, Puccinia hordei, Gibberella zeae, Pyrenophorateres, Typhula incarnata, Typhula ishikariensis, Sclerotiniaborealis, Micronectriella nivalis, Ustilagonuda, Tilletia caries, Tilletia toetida, Tapesia yallundea, Phynchosporium secalis* f. sp. *hordei, Septoria tritici,* and *Lentosphaeria nodorum*; with respect to citrus *Diaporthe citri, Elsinoe fawcettii, Phytophthora citrophthora, Penicillium digitatum* and *Penicillium italicum*; with respect to apple *Monilinia mali, Valsa ceratosperma, Podosphaera leucotricha, Alternaria alternataapple* pathotype, *Venturia inaequalis, Gymnosporangium yamadae, Botriophaeria berengeriana* f. sp. *piricola, Zygophiala jamaicensis, Gloeodes pomigena, Mycosphaerella pomi, Glomerella cingulate,* and *Diplocarponmali*; with respect to pear *Venturia nashicola, Alternaria alternata* japanese pear pathotype, *Physalospora piricola,* and *Gymnosporangium asiaticum*; with respect to peach *Monilinia fructicola, Cladosporium carpophilum,* and *Phomopsis* sp.; with respect to grape *Pseudocercospora vitis, Marssonina viticola, Elsinoe ampelina, Glomerella cingulata, Uncinula necator, Phakopsora ampelopsidis,* and *Phomopsis* sp.; with respect to kaki *Phyllactinia kakicola, Colletotrichum gloeosporioides, Cercospora kaki,* and *Mycosphaerella nawae*; with respect to plum *Cladosporium carpophilum*; with respect to cherry *Monilinia fructicola*; with respect to gourd *Sphaerotheca fuliginea, Didymella bryoniae,* and *Colletotorichum legenarium*; with respect to tomato *Alternaria solani,* and *Cladosporium fulvum*; with respect to eggplant *Phomopsis vexans,* and *Erysiphe cichoracearum*; with respect to brassica family vegetable *Alternaria japonica, Alternaria bracicae, Alternaria brassicicola,* and *Cercosporella brassicae*; with respect to green onion *Pucciniaallii*; with respect to ginger *Pyrhium ultimum,* and *Pythium zigiberis*; with respect to strawberry *Sphaerotheca humuli,* and *Glomerella cingulate*; with respect to soybean *Cercospora kikuchii, Elsinoe glycines,* and *Diaporthe phaseolorum* var. *sojae*; with respect to adzuki bean *Cercospora canescens,* and *Uromyces phaseoli* var. *azukicola*; with respect to kidney bean *Colletotrichum lindemuthianum*; with respect to peanut *Cercosporidium personatum, Cercospora arachidicola,* and *Shacelomna arachidis*; with respect to pea *Erysiphe pisi*; with respect to potato *Alternaria solani*; with respect to tea plant *Exobasidium reticulatum, Elsinoe leucospila, Pestalotiopsis theae,* and *Pestalotiopsis longiseta*; with respect to tobacco *Alternaria longipes, Erysiphe cichoracearum,* and *Colletotrichum gloeosporioides*; with respect to beet *Cercospora beticola*; with respect to lawn grass *Curvularia geniculate,* and *Ceratobasidium* spp.; with respect to rose *Diplocarpon rosae,* and *Shaerotheca pannosa*; with respect to chrysanthemum *Septoria obesa,* and *Puccinia horiana*; and with respect to various crop plants *Botrytis cinerea,* and *Sclerotinia sclerotiorum.*

Examples of nematodes that a microorganism according to the present invention can control include, but not limited to, especially plant-parasitic nematodes like root-knot nematodes, such as *Meloidogyne hapla, Meloidogyne incognila, Meloidogyne javanica,* and other *Meloidogyne* species; cyst forming nematodes, such as *Globodera roslochiensis,* and other *Globodera* species; *Heterodera avenae, Heterodera glycines, Heterodera schachtii, Heterodera trifolii,* and other *Heterodera* species; seed gall nematodes, such as *Anguiana* species; stem and foliar nematodes, such as *Aphelenchoides* species; sting nematodes, such as *Belonolaimus longicaudatus* and other *Belonolaimus* species; pine nematodes, such as *Bursaphelenchus xylophilus,* and other *Bursaphelenchus* species; ring nematodes, such as *Criconema* species, *Criconemella* species, *Criconemoides* species, and *Mesocriconema* species; stem and bulb nematodes, such as *Ditylenchus destructor, Ditylenchus dipsaci,* and other *Ditylenchus* species; awl nematodes, such as *Dolichodorus* species; spiral nematodes, such as *Heliocotylenchus multicinctus,* and other *Helicotylenchus* species; sheath and sheathoid nematodes, such as *Hemicycliophora* species, and *Hemicriconemoides* species; *Hirshmanniella* species; lance nematodes, such as *Hoploaimus* species; false root-knot nematodes, such as *Nacobbus* species; needle nematodes, such as *Longidorus elongates,* and other *Longidorus* species; meadow nematodes, such as *Pratylenchus neglectus, Pratylenchus penetrans, Pratylenchus curvitatus, Pratylenchus goodeyi,* and other *Pratylenchus* species; burrowing nematodes, such as *Radopholus similis,* and other *Radopholus* species; reniform nematodes, such as *Rotylenchus robustus,* and other *Rotylenchus* species; *Scutellonema* species; stubby root nematodes, such as *Trichodorusprimitivus,* other *Trichodorus* species, and *Paratrichodorus* species; stunt nematodes, such as *Tylenchorhynchus claytoni, Tylenchorhynchus dubius,* and other *Tylenchorhynchus* species; citrus nematodes, such as *Tylenchulus* species; and dagger nematodes, such as *Xiphinema* species.

Although it is preferable that the microorganism is applied to a plant before the nematodes are attached to the plant so as to prevent a disease, it may also be applied to a plant having been infected with the nematodes for removing the nematodes.

For a microbiological formulation according to the present invention (plant disease controlling agent, nematode controlling agent, and plant growth promoting agent), bacterial cells and/or a culture product may be used alone, or a preparation, in which the same is diluted with an inert liquid or a solid support, and to which, if necessary, a surfactant, a dispersing agent, and other auxiliary agents are added, may be used. Specific examples of the preparation include such dosage forms as a granular form, a powder form, a water-dispersible powder form, a suspension form, and an emulsion form.

Examples of a support include porous solid supports, such as talc, bentonite, kaolin, clay, diatomaceous earth, white carbon, vermiculite, slaked lime, ammonium sulfate, silica sand, and urea, and liquid carriers, such as water, isopropyl alcohol, methyl naphthalene, xylene, cyclohexanone, and an alkylene glycol. Examples of a surfactant and a dispersing agent include a dinaphthyl methane sulfonic acid salt, an alcohol sulfuric acid ester salt, a lignin sulfonic acid salt, an alkylarylsulfonic acid salt, polyoxyethylene glycol ether, a polyoxyethylene sorbitan monoalkylate, and a polyoxyethylene alkyl aryl ether. Examples of an auxiliary agent include carboxymethyl cellulose, polyethylene glycol, propylene glycol, gum arabic, and xanthan gum, and examples of a protective agent include skimmed milk, and a pH buffer agent. In this case, the content of living cells of a strain and/or the content of the culture product, and also the application time and the dosage may be determined appropriately following the case of single use of living cells.

Examples of a liquid carrier include a phosphate buffer solution, a carbonate buffer solution, and a physiological saline solution. Examples of a solid support include natural mineral powders, such as kaolin, clay, talc, chalk, quartz, attapulgite, montmorillonite, and diatomaceous earth, synthetic mineral powders, such as silica, alumina, and silicate, and macromolecular natural products, such as crystalline cellulose, cornstarch, gelatin, andalginicacid. Examples of a surfactant include a polyoxyethylene-fatty acid ester, a polyoxyethylene-fatty alcohol ether, an alkylaryl polyglycol ether, an alkyl sulfonate, an alkyl sulfate, and an aryl sulfonate. Examples of an auxiliary agent include carboxymethyl cellulose, polyoxyethyleneglycol, gum arabic, starch, and milk sugar.

When a liquid formulation is prepared with an aqueous solvent as a carrier, a water soluble polymer may be added in order to improve the wettability of a bacterial cell in the solvent. Examples of a water soluble polymer include poly (vinyl alcohol), poly(ethylene glycol), poly(vinyl methyl ether), polyvinylamine, polyvinylpyrrolidone, polyethyleneimine, and poly(acrylic amide). Further, a polysaccharide, such as xyloglucan, and guar gum, may be added in order to improve the adhesiveness of the microorganism of the present invention to a plant root, and the stability of the microorganism of the present invention in a formulation.

Although there is no particular restriction on the concentration of a microorganism according to the present invention contained in a microbiological formulation according to the present invention insofar as the effect as a plant disease controlling agent, a nematode controlling agent and/or a plant growth promoting agent is not impaired, the concentration in a formulation is $10^5$ to $10^{13}$ cfu/g (colony formation unit), and preferably $10^7$ to $10^{12}$ cfu/g. The same may be changed appropriately depending on the controlling effect of a used microorganism according to the present invention, or the severity of a disease.

A microbiological formulation according to the present invention may contain an optional substance such as a culture medium used for the culture of a microorganism according to the present invention in addition to the above substances, insofar as the effect of the present invention is not impaired.

Although there is no particular restriction on an application method of a microbiological formulation according to the present invention, it is selected appropriately depending on a type of application, such as a dosage form, a crop, and a disease. Examples of an application method include ground application of a liquid, ground application of a solid, aerial application of a liquid, aerial application of a solid, water surface application, intra-institution application, soil incorporation application, soil irrigation application, surface treatment (seed powder coating, painting treatment, etc.), a nursery box method, an individual flower treatment, and a plant foot treatment, and examples of a preferable method include a method in which the microbiological formulation of any of various dosage forms is coated on a seed or a seed potato of a plant to be cultivated, a method in which an individual flower of a cultivated plant is treated with the formulation, a method in which a stem and leaf of a cultivated plant is treated with the formulation, a method in which a wound site or a trimmed part of a cultivated plant is coated with the formulation, a method of soil irrigation, and a method of soil mix. In this regard, when a formulation is applied to soil, a cultivated plant may be planted after a microbiological formulation according to the present invention is applied to the soil, or a microbiological formulation according to the present invention may be applied to the soil, after a cultivated plant was planted.

A microbiological formulation according to the present invention is preferably sprayed on a stem and leaf in order to control a stem and leaf disease. A microbiological formulation according to the present invention is preferably sprayed or irrigated in order to control a soil disease.

A microbiological formulation according to the present invention (plant disease controlling agent, nematode controlling agent, and plant growth promoting agent) may contain, if necessary, an active ingredient other than an active ingredient according to the present invention, for example an insecticidal agent, another bactericidal agent, a herbicidal agent, a plant growth regulating agent, and a fertilizer.

Examples of a bactericidal component include, but not limited to, bitertanol, bromuconazole, cyproconazole, difenoconazole, diniconazole, enilconazole, epoxiconazole, fluquinconazole, fenbuconazole, flusilazole, flutriafol, hexaconazole, imibenconazole, ipconazole, metconazole, myclobutanil, penconazole, propiconazole, prothioconazole, simeconazole, triadimefon, triadimenol, tebuconazole, tetraconazole, triticonazole, prochloraz, pefurazoate, imazalil, triflumizole, cyazofamid, benomyl, carbendazim, thiabendazole, fuberidazole, ethaboxam, etridiazole, oxypoconazole fumaric acid, himexazole, azoxystrobin, dimoxystrobin, enestroburin, fluoxastrobin, kresoxym-methyl, metominostrobin, oryzastrobin, picoxystrobin, pyraclostrobin, trifloxystrobin, carboxin, benalaxyl, boscalid, bixafen, fenhexamid, flutolanil, furametpyr, mepronil, metalaxyl, mefenoxam, ofurace, oxadixyl, oxycarboxin, penthiopyrad, thifluzamide, tianidil, dimethomorph, flumorph, flumetover, fluopicolide, carpropamid, diclocymet, mandipropamid, fluazinam, pyrifenox, bupirimate, cyprodinil, fenarimol, ferimzone, mepanipyrim, nuarimol, pyrimethanil, triforine, fenpiclonil, fludioxonil, aldimorph, dodemorph, fenpropimorph, tridemorph, fenpropidin, iprodione, procymidone, vinclozolin, famoxadone, fenamidone, octhilinone, probenazole, anilazine, diclomezine, pyroquilon, proquinazid, tricyclazole, captafol, captan, dazomet, folpet, fenoxanil, quinoxyfen, amisulbrom, manzeb, maneb, metam, metiram, ferbam, propineb, thiuram, zineb, ziram, diethofencarb, iprovalicarb, benthiavalicarb-isopropyl, propamocarb hydrochloride, thiophanate-methyl, pyribencarb, Bordeaux mixture, basic copper chloride, basic copper sulfide, cupric hydroxide, copper 8-hydroxyquinoline, dodine, iminoctadine albesilate, iminoctadine acetate, guazatine, kasugamycin, streptomycin, polyoxin, oxytetracycline, validamycin A, binapacryl, dinocap, dinobuton, dithianon, isoprothiolane, edifenphos, iprobenfos, fosetyl, fosetyl aluminum, pyrazophos, tolclofos-methyl, chlorothalonil, dichlofluanid, flusulfamide, hexyachlorobenzene, phthalide, pencycuron, quintozene, cyflufenamid, cymoxanil, dimethirimol, ethyrimol, furalaxyl, metrafenone, spiroxamine, amobam, sulfur, lime sulfur, echlomezole, potassium bicarbonate, calcium bicarbonate, thiadiazine, tecloftalam, triazine, copper nonylphenol sulfonate, hydroxy isoxazole, fluoroimide, polycarbamate, methasulfocarb, EDDP, IBP, tolfenpyrad, fluopyram, isotianil and isopyrazam.

Examples of an insecticidal component include, but not limited to, acetamiprid, pymetrozine, fenitrothion, acephate, carbaryl, methomyl, cartap, cyhalothrin, ethofenprox, teflubenzuron, flubendiamide, flufenoxuron, tebufenozide, fenpyroximate, pyridaben, imidacloprid, buprofezin, BPMC, MIPC, malathion, methidathion, fenthion, daiazinon, oxydeprofos, vamidothion, ethiofencarb, pirimicarb, permethrin, cypermethrin, bifenthrin, halfenprox, silaflu-ofen, nitenpyram, chlorfluazuron, methoxyfenozide, tebufenpyrad, pyrimidifen, kelthane, propargite, hexythiazox, clofentezine, spinosad, milbemectin, BT (*Bacillus thuringiensis*), indoxacarb, metaflumizone, chlorfenapyr, fipronil, etoxazole, acequinocyl, pirimiphos-methyl, acrinathrin, quinomethionate, chlorpyrifos, abamectin, emamectin benzoate, fenbutatin oxide, terbufos, ethoprophos, cadusafos, fenamiphos, fensulfothion, DSP, dichlofenthion, fosthiazate, oxamyl, isoamidofos, fosthietan, isazophos, thionazin, benfuracarb, spirodiclofen, ethiofencarb, azinphos-methyl, disulfoton, methiocarb, oxydemeton-methyl, parathion, cyfluthrin, beta-cyfluthrin, tebupirimfos, spiromesifen, endosulfan, amitraz, tralomethrin, acetoprole, ethiprole, ethion, triclorfon, methamidophos, dichlorvos, mevinphos, monocrotophos, dimethoate, formetanate, formothion, mecarbam, thiometon, disulfoton, naled, methyl parathion, cyanophos, diamidafos, albendazole, oxibendazole, fenbendazole, oxfendazole, propaphos, sulprofos, prothiofos, profenofos, isofenphos, temephos, phenthoate, dimethylvinphos, chlorfenvinphos, tetrachlorvinphos, phoxim, isoxathion, pyraclofos, chlorpyrifos, pyridaphenthion, phosalone, phosmet, dioxabenzofos, quinalphos, pyrethrin, allethrin, prallethrin, resmethrin, permethrin, tefluthrin, fenpropathrin, alpha-cypermethrin, lambda-cyhalothrin, deltamethrin, fenvalerate, esfenvalerate, flucythrinate, fluvalinate, cycloprothrin, thiodicarb, aldicarb, alanycarb, metolcarb, xylylcarb, propoxur, fenoxycarb, fenothiocarb, bifenazate, carbofuran, carbosulfan, sulfur, pyrifluquinazon, furathiocarb, diafenthiuron, diflubenzuron, hexaflumuron, novaluron, lufenuron, chlorfluazuron, tricyclohexyltin hydroxide, sodium oleate, potassium oleate, methoprene, hydroprene, binapacryl, amitraz, chlorobenzilate, pheniso-bromolate, tetradifon, bensultap, benzomate, chromafenozide, halofenozide, endosulfan, diofenolan, tolfenpyrad, triazamate, nicotine sulfate, thiacloprid, thiamethoxam, clothianidin, dinotefuran, fluazinam, pyriproxyfen, fluacrypyrim, hydramethylnon, cyromazine, TPIC, thiocyclam, fenazaquin, a polynactin complex, azadirachtin, rotenone, hydroxypropyl starch, mesulfenphos, phosphocarb, isoamidofos, aldoxycarb, metham sodium, morantel tartrate, dazomet, levamisole hydrochloride, trichlamide, tolfenpyrad, pyridalyl, chlorantraniliprole, cyenopyrafen, and cyflumetofen.

EXAMPLES

The present invention will be described more specifically below referring to Examples, provided that the technical scope of the present invention be not limited to the Examples.

Microorganisms were isolated from a soil including plant roots collected in Japan. Specifically, 1 g of dry soil obtained by a heat treatment (80° C., 10 min) of the collected soil was suspended in sterilized water. The suspension was diluted $10^2$ to $10^4$-fold and subjected to an isolation culture (28° C., 3 days) with a nutrient agar (Eiken Chemical Co., Ltd.), and then formed colonies were isolated. From the isolated colonies, strains having effectiveness on various various plant pathogens on a potato-dextrose agar were identified. As the results, 4 kinds of microorganisms were obtained and designated as ITB090 (NITE BP-01725), ITB100 (NITE BP-01726), ITB105 (NITE BP-01727), and ITB117 (NITE P-01728) respectively. The sequence of a 16S rRNA gene with respect to each of the microorganisms was examined for phylogenetic analysis, and all of them were identified as *Bacillus* sp.

The microorganisms were evaluated with respect to plant disease control activity, nematocidal activity, and plant growth promotion effect according to the following procedures.

Example 1

In Vitro Test for Plant Disease Controlling Effect
(1) Culture Method for Various Bacteria With respect to each of ITB090 (NITE BP-01725), ITB100 (NITE BP-01726), ITB105 (NITE BP-01727), and ITB117 (NITE P-01728) strains, one loopful of preserved bacterial cells was inoculated into a 500 mL Erlenmeyer flask with a baffle containing 60 mL of a nutrient broth (Eiken Chemical Co., Ltd.), and the content was cultured with shaking by a rotary shaker at a rotating speed of 180 rpm, at 28° C. for 2 days. The obtained culture solution was diluted with sterilized water to $5 \times 10^7$ cfu/mL and subjected to a dual culture test.
(2) Dual Culture Method At an edge of a dish containing a potato-dextrose agar, 20 μL each of the diluted culture solution was inoculated. Hyphae of various plant pathogens (damping-off disease: *Rhizoctonia solani*, Alternaria blotch disease: *Alternaria mali*, anthracnose: *Glomerella* cingulate, blast disease: *Pyricularia oryzae*, and gray mold disease: *Botrytis cinerea*) cultured in advance were taken out together with a culture medium by boring with a 5 mm-diameter cork borer and inoculated to the center of the dish. The dish was incubated at 25° C. for 2 to 5 days, and an antagonistic action or formation of an inhibition zone was observed with respect to each of various pathogens.

(3) Investigation Method

When an antagonistic action or formation of an inhibition zone was observed with respect to each of various pathogens, it was denoted as "+", and when the same was not observed, it was denoted as "−".

(4) Results

The investigation results are shown in Table 1. It has become clear that the novel strains according to the present invention have controlling activity on the pathogens tested.

TABLE 1

|  | Damping off | *Alternaria* blotch | Anthracnose | Blast | Gray mold |
|---|---|---|---|---|---|
| ITB090 | + | + | + | + | + |
| ITB100 | + | + | + | + | + |
| ITB105 | + | + | + | + | + |
| ITB117 | − | + | + | − | − |

Example 2

Test of Controlling Effect on Cucumber Gray Mold Disease (*Botrytis cinerea*)

(1) Culture Method of Various Bacteria

With respect to each of ITB090 (NITE BP-01725), ITB100 (NITE BP-01726), ITB105 (NITE BP-01727), and ITB117 (NITE P-01728) strains, one loopful of preserved bacterial cells was inoculated into a 500 mL Erlenmeyer flask with a baffle containing 60 mL of a nutrient broth (Eiken Chemical Co., Ltd.), and the content was cultured with shaking by a rotary shaker at a rotating speed of 180 rpm, at 28° C. for 2 days. The obtained culture solution was diluted with sterilized water to $5 \times 10^7$ cfu/mL and subjected to a next test. As a reference, *Bacillus subtilis* MBI600 (purchased and isolated from Botokiller Wettable Powder (Idemitsu Kosan Co., Ltd.)) was cultured identically.

(2) Treatment Method

A fully expanded cucumber seed leaf (Tokiwa-Hikari No. 3, P-Type) was cut off at a hypocotyl, and the cut surface was contacted with a wet paper towel. An inoculum was prepared by suspending spores of a gray mold disease fungus cultured in a PSA medium in 5 mL of a PS medium. To the center of the seed leaf, 50 μL of the gray mold disease bacterium spore suspension was dropped. On a water droplet formed by dropping, a piece of Paper Discs (paper disks for antibiotic assay, thick type, 8 mmΦ, Toyo Roshi Kaisha, Ltd.) was placed, to which 50 μL of a test agent (a cell suspension with a concentration of $5 \times 10^7$ cfu/mL) was dropped, and the sample was stored carefully in a moist chamber at 25° C.

(3) Investigation Method

A lesion area appeared on the cucumber leaf on day 3 after the inoculation was examined, and a preventive value was determined according to the following formula (1):

Preventive value={1−(lesion area in treated region/lesion area in untreated region)}×100      Formula (1)

TABLE 2

|  | Preventive value |
|---|---|
| ITB090 | 100 |
| ITB100 | 100 |
| ITB105 | 96 |

TABLE 2-continued

|  | Preventive value |
|---|---|
| ITB117 | 98 |
| MBI600 | 80 |

As obvious from the results shown in Table 2, the incidence rate of a cucumber gray mold disease due to *Botrytis cinerea* was reduced remarkably by a treatment with a microorganism according to the present invention compared to an untreated control, and an extremely high controlling effect compared to with the *Bacillus subtilis* MBI600 strain was obtained.

Example 3

Nematode Controlling Effect (1) Culture Method of Various Bacteria

With respect to each of ITB090 (NITE BP-01725), ITB100 (NITE BP-01726), ITB105 (NITE BP-01727), and ITB117 (NITE P-01728) strains, one loopful of preserved bacterial cells was inoculated into a 500 mL Erlenmeyer flask with a baffle containing 60 mL of a nutrient broth (Eiken Chemical Co., Ltd.), and the content was cultured with shaking by a rotary shaker at a rotating speed of 180 rpm, at 28° C. for 2 days. The obtained culture solution was diluted with sterilized water to $5 \times 10^7$ cfu/mL and subjected to a test.

As a reference case, a *Bacillus subtilis* MBI600 strain (purchased and isolated from Botokiller Wettable Powder (Idemitsu Kosan Co., Ltd.)) was cultured identically and used for the test.

(2) Test Method for Nematocidal Activity

The nematocidal activity on a second-stage larva of a sweet-potato root-knot nematode (*Meloidogyne incognita*) hatched within 24 hours from an egg capsule collected from a tomato root was tested. Diluted culture solutions of various bacteria and equivalents of a suspension of root-knot nematode second-stage larvae (about 50 worms) were added to a microplate. As a comparative agent, a *Bacillus subtilis* MBI600 strain (purchased and isolated from Botokiller Wettable Powder (Idemitsu Kosan Co., Ltd.)) suspension diluted identically was tested. The plate was closed tightly and placed into an incubator at 28° C. and relative humidity of approx. 50%

(3) Investigation Method

After 72 hours, the death rate of the nematode was investigated by an observation under a stereoscopic microscope. In doing so, immobile nematodes were deemed as dead. The nematicidal rate was calculated according to the following Formula (2):

Nematocidal rate (%)=(Number of dead nematodes/Number of tested nematodes)×100      Formula (2)

(4) Results

As obvious from the results shown in Table 3, very high nematocidal activities on the sweet-potato root-knot nematode second-stage larvae was obtained by a treatment with a microorganism according to the present invention compared to with the *Bacillus subtilis* MBI600 strain.

TABLE 3

|  | Nematocidal rate % |
|---|---|
| ITB090 | 100 |
| ITB100 | 100 |

TABLE 3-continued

| | Nematocidal rate % |
|---|---|
| ITB105 | 60 |
| ITB117 | 50 |
| MBI600 | 10 |

Example 4

Test of Controlling Effect on Sweet-Potato Root-Knot Nematode
(1) Culture Method of Various Bacteria With respect to each of ITB090 (NITE BP-01725), ITB100 (NITE BP-01726), ITB105 (NITE BP-01727), and ITB117 (NITE P-01728) strains, one loopful of preserved bacterial cells was inoculated into a 500 mL Erlenmeyer flask with a baffle containing 60 mL of a nutrient broth (Eiken Chemical Co., Ltd.), and the content was cultured with shaking by a rotary shaker at a rotating speed of 180 rpm, at 28° C. for 2 days. The obtained culture solution was diluted with sterilized water to $5\times10^7$ cfu/mL and subjected to a next test. As a reference, Bacillus subtilis MBI600 strain (purchased and isolated from Botokiller Wettable Powder (Idemitsu Kosan Co., Ltd.)) was cultured identically.
(2) Treatment Method The obtained culture solution was diluted with sterilized water to $1\times10^7$ cfu/mL, and cucumber seeds (Tokiwa-Hikari No. 3, P-Type) were immersed therein for 30 min and then seeded in a 1/10000a Wagner pot filled with a soil contaminated with root-knot nematodes at a density of approx. 3.3 root-knot nematodes per 20 g of dry soil.
(3) Investigation Method The degree of infestation of root-knots was evaluated according to the following class values rated by the degree of damage of a root (degree of root-knot) after 1 month from seeding according to a method of Zeck (Zeck, W. M. (1971): Pflanzenschutz-Nachichten, Bayer AG, 24, 141-144).
0: Root-knot is not recognized at all.
1: Root-knots are recognized by careful observation.
2: Several small root-knots similarly as 1 above are easily recognizable.
3: There are a large number of small root-knots, and some of which have fused together. The function of roots has been almost not impaired.
4: There are a large number of small of root-knots, and are some large root-knots. Most of roots are functioning.
5: Root-knots have developed remarkably in 25% of roots, and the roots are not functioning.
6: Root-knots have developed remarkably in 50% of roots, and the roots are not functioning.
7: Root-knots have developed remarkably in 75% of roots, and the regenerative capacity of roots has been lost.
8: There is no sound root, and the nutrient absorption of the plant has been inhibited. The stem and leaf part is still green.
9: The root system completely covered with root-knots is decaying. The plant is dying.
10: The plant and roots have died.

A root-knot index was determined according to the following Formula (3):

Root-knot index=Σ(Degree of damage×Number of individuals)/(Total number of investigated individuals×10)×100   Formula (3)

Based on the evaluated degree of development of root-knots, a preventive value was calculated according to the following Formula (4):

Preventive value=100−(Root-knot index in treated case/Root-knot index in untreated case)×100   Formula (4)

TABLE 4

| | Root-knot index | Preventive value |
|---|---|---|
| No treatment | 44.2 | — |
| ITB090 | 18.0 | 59.4 |
| ITB100 | 14.8 | 66.4 |
| ITB105 | 18.6 | 57.9 |
| ITB117 | 19.4 | 56.1 |
| MBI600 | 21.9 | 50.4 |

As obvious from the results shown in Table 4, the root-knot index due to a sweet-potato root-knot nematode was reduced remarkably by a treatment with a microorganism according to the present invention compared to an untreated case, and an extremely high controlling effect compared to the Bacillus subtilis MBI600 strain was obtained.

Example 5

Plant Growth Promotion Effect
(1) Culture Method of Various Bacteria

With respect to each of ITB090 (NITE BP-01725), ITB100 (NITE BP-01726), ITB105 (NITE BP-01727), and ITB117 (NITE P-01728) strains, one loopful of preserved bacterial cells was inoculated into a 500 mL Erlenmeyer flask with a baffle containing 60 mL of a nutrient broth (Eiken Chemical Co., Ltd.), and the content was cultured with shaking by a rotary shaker at a rotating speed of 180 rpm, at 28° C. for 2 days. As a reference, Bacillus subtilis MBI600 (purchased and isolated from Botokiller Wettable Powder (Idemitsu Kosan Co., Ltd.)) was cultured identically.
(2) Treatment Methods of Respective Bacteria Treatment Method for Wheat The obtained culture solution was diluted with sterilized water to $1\times10^7$ cfu/mL, and wheat seeds were immersed therein for 30 min, and then seeded in a pot filled with a nursery soil.
Treatment Method for Arabidopsis thaliana Arabidopsis thaliana was seeded in a pot filled with a nursery soil, and then the obtained culture solution was diluted with sterilized water to $1\times10^7$ cfu/mL, and 5 mL thereof was irrigated.
Treatment Method for Maize The obtained culture solution and maize seeds were mixed to $1\times10^8$ cfu per 1 g of seeds, so as to apply each of the culture solutions to the seeds. The treated seeds were seeded in a pot filled with a nursery soil.
Treatment Method for Soybean The obtained culture solution and soybean seeds were mixed to $1\times10^7$ cfu per 1 g of seeds, so as to apply each of the culture solutions to the seeds. The treated seeds were seeded in a pot filled with a nursery soil.
(3) Investigation Method Wheat: The terrestrial weight per plant was measured 3 weeks after the seeding.

Arabidopsis thaliana: The leaf area per plant was measured 3 weeks after the seeding.

Maize: The terrestrial weight per plant was measured 4 weeks after the seeding.

Soybean: The terrestrial weight per plant was measured 4 weeks after the seeding.

Increased amounts with respect to the untreated control were calculated.

(4) Results

The results are shown in the following Table 5. With respect to all the plants, plant growth was remarkably promoted by a treatment of each strain compared to the untreated control, and growth promotion effects extremely higher than the same of the *Bacillus subtilis* MBI600 strain were exhibited.

TABLE 5-1

Wheat: Wet weight (%) relative to untreated control

| Strain | Wheat |
|---|---|
| ITB090 | 122% |
| ITB100 | 134% |
| ITB105 | 131% |
| ITB117 | 117% |
| MBI600 | 108% |

TABLE 5-2

*Arabidopsis thaliana*: Leaf area (%) relative to untreated control

| Strain | *Arabidopsis thaliana* |
|---|---|
| ITB090 | 117% |
| ITB100 | 122% |
| ITB105 | 120% |

TABLE 5-2-continued

*Arabidopsis thaliana*: Leaf area (%) relative to untreated control

| Strain | *Arabidopsis thaliana* |
|---|---|
| ITB117 | 114% |
| MBI600 | 112% |

TABLE 5-3

Maize: Wet weight (%) relative to untreated control

| Strain | Maize |
|---|---|
| ITB090 | 106% |
| ITB100 | 131% |
| ITB105 | 144% |
| ITB117 | 108% |
| MBI600 | 104% |

TABLE 5-4

Soybean: Wet weight (%) relative to untreated control

| Strain | Soybean |
|---|---|
| ITB090 | 105% |
| ITB100 | 125% |
| ITB105 | 130% |
| ITB117 | 125% |
| MBI600 | 102% |

The invention claimed is:

1. A method of promoting plant growth, comprising:
   treating a seed of a plant with bacterial cells or a culture product including bacterial cells of *Bacillus* sp. ITB105 strain NITE BP-01727,
   wherein the *Bacillus* sp. ITB105 strain NITE BP-01727 has the 16S rDNA having the nucleotide sequence of SEQ ID NO: 3.

2. The method according to claim 1, wherein the seed is a seed of at least one selected from the group consisting of wheat, corn, and soybean.

3. The method according to claim 1, wherein the treating comprises contacting a culture solution including bacterial cells of the *Bacillus* sp. ITB105 strain NITE BP-01727 to a surface of the seed.

4. The method according to claim 2, wherein the treating comprises contacting a culture solution including bacterial cells of the *Bacillus* sp. ITB105 strain NITE BP-01727 to a surface of the seed.

5. The method according to claim 3, wherein the culture solution contains $10^7$ to $10^{12}$ cfu/g of the *Bacillus* sp. ITB105 strain NITE BP-01727.

6. The method according to claim 4, wherein the culture solution contains $10^7$ to $10^{12}$ cfu/g of the *Bacillus* sp. ITB105 strain NITE BP-01727.

7. The method according to claim 1, wherein the treating comprises performing one of powder coating of the seed with the bacterial cells, an immersion treatment of the seed into a culture solution including the bacterial cells, and a painting treatment of the seed with the culture solution.

8. The method according to claim 2, wherein the treating comprises performing one of powder coating of the seed with the bacterial cells, an immersion treatment of the seed into a culture solution including the bacterial cells, and a painting treatment of the seed with the culture solution.

9. The method according to claim 1, wherein the treating is performed such that the plant is produced with an increased yield as a result of the growth promotion.

10. The method according to claim 2, wherein the treating is performed such that the plant is produced with an increased yield as a result of the growth promotion.

11. The method according to claim 1, wherein the treating is performed such that the plant is cultivated with an increased leaf area as a result of the growth promotion.

12. The method according to claim 2, wherein the treating is performed such that the plant is cultivated with an increased leaf area as a result of the growth promotion.

13. The method according to claim 1, wherein the treating is performed such that the plant is produced with an increase in a weight and a thickness of a terrestrial stem and leaf of the plant as a result of the growth promotion.

14. The method according to claim 2, wherein the treating is performed such that the plant is produced with an increase in a weight and a thickness of a terrestrial stem and leaf of the plant as a result of the growth promotion.

15. The method according to claim 2, wherein the treating comprises performing powder coating of the seed with the bacterial cells.

16. The method according to claim 2, wherein the treating comprises performing an immersion treatment of the seed into a culture solution including the bacterial cells.

17. The method according to claim 2, wherein the treating comprises performing a painting treatment of the seed with a culture solution including the bacterial cells.

18. The method according to claim 16, wherein the culture solution includes $10^7$ to $10^{12}$ cfu/g of the *Bacillus* sp. ITB105 strain NITE BP-01727.

19. The method according to claim 16, wherein the culture solution includes $10^7$ to $10^8$ cfu/g of the *Bacillus* sp. ITB105 strain NITE BP-01727.

20. The method according to claim 17, wherein the culture solution includes $10^7$ to $10^8$ cfu/g of the *Bacillus* sp. ITB105 strain NITE BP-01727.

\* \* \* \* \*